United States Patent
Das et al.

(10) Patent No.: US 11,220,711 B2
(45) Date of Patent: Jan. 11, 2022

(54) COMPOSITIONS FOR CHARACTERIZING DEVELOPMENT OF ESOPHAGEAL ADENOCARCINOMA IN PATIENTS AND METHODS OF USE THEREOF

(71) Applicant: Rutgers, The State University of New Jersey, New Brunswick, NJ (US)

(72) Inventors: Kiron Das, Basking Ridge, NJ (US); Manisha Bajpai, Hillsborough, NJ (US); Hana Aviv, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 186 days.

(21) Appl. No.: 16/083,055

(22) PCT Filed: Mar. 8, 2017

(86) PCT No.: PCT/US2017/021405
§ 371 (c)(1),
(2) Date: Sep. 7, 2018

(87) PCT Pub. No.: WO2017/156154
PCT Pub. Date: Sep. 14, 2017

(65) Prior Publication Data
US 2019/0100803 A1    Apr. 4, 2019

Related U.S. Application Data

(60) Provisional application No. 62/305,194, filed on Mar. 8, 2016.

(51) Int. Cl.
| | | |
|---|---|---|
| *C12Q 1/68* | (2018.01) | |
| *C12P 19/34* | (2006.01) | |
| *C12Q 1/6883* | (2018.01) | |
| *G01N 33/573* | (2006.01) | |
| *G01N 33/53* | (2006.01) | |
| *G01N 33/574* | (2006.01) | |
| *C12Q 1/6837* | (2018.01) | |

(52) U.S. Cl.
CPC ............ *C12Q 1/6883* (2013.01); *C12Q 1/68* (2013.01); *C12Q 1/6837* (2013.01); *G01N 33/53* (2013.01); *G01N 33/573* (2013.01); *G01N 33/574* (2013.01); *C12Q 2600/112* (2013.01); *C12Q 2600/156* (2013.01); *C12Q 2600/16* (2013.01)

(58) Field of Classification Search
CPC .. C12Q 1/6883; C12Q 1/68; C12Q 2600/112; G01N 33/574
See application file for complete search history.

(56) References Cited

U.S. PATENT DOCUMENTS

| | | |
|---|---|---|
| 6,812,339 B1 | 11/2004 | Venter et al. |
| 2004/0152125 A1 | 8/2004 | Presnell et al. |
| 2009/0226933 A1 | 9/2009 | Albitar et al. |

FOREIGN PATENT DOCUMENTS

WO    2014071419 A2    5/2014

OTHER PUBLICATIONS

Jin, Y. et al, "Cytogenetic and fluorescence in situ hybridization characterization of clonal chromosomal aberrations and CCND1 amplification in esophageal carcinomas" Cancer Genetics and Cytogenetics 148 (2004) 21-28 (Year: 2004).*
Liu, F. et al. "Dissecting the mechanism of colorectal tumorigenesis based on RNA-sequencing data" Experimental and Molecular Pathology. vol. 98, Issue 2, Apr. 2015, pp. 246-253 (available online Jan. 7, 2015) (Year: 2015).*
International Search Report and Written Opinion dated Apr. 6, 2018, issued by the U.S. Patent and Trademark Office in International Application No. PCT/US17/021405 (22 pages).
Bajpai, Manisha et al., "Prolonged exposures to acid and bile induces chromosome abnormalities that precede malignant transformation of benign Barrett's epithelium", Molecular Cytogenetics, pp. 1-8 (2012), http://www.molecularcytogenetics.org/content/5/1/43.

* cited by examiner

Primary Examiner — Stephen T Kapushoc
(74) Attorney, Agent, or Firm — Greenberg Traurig, LLP

(57) ABSTRACT

The present invention is a method, comprising: obtaining a sample of an esophageal tissue from a subject, wherein the sample of the esophageal tissue comprises or is suspected of comprising a break of chromosome 2 (chr2), a break of chromosome 10 (chr10), a break of chromosome 16 (chr16), or any combination thereof, and detecting in the sample of esophageal tissue whether the break of chr2 is present, whether the break of chr10 is present, whether the break of chr16 is present, or any combination thereof, by contacting the sample of esophageal tissue with a first detectably labeled probe, a second detectably labeled probe, a third detectably labeled probe, or any combination thereof, and detecting binding between: the first detectably labeled probe and the break of chr2, the second detectably labeled probe and the break of chr10, the third detectably labeled probe and the break of chr16, or any combination thereof.

8 Claims, 5 Drawing Sheets

Specification includes a Sequence Listing.

Das K.M. et.al., Int. J. Cancer: 128, 274-282 (2011)

Bajpai M, et.al., Lab Invest: 88:643-51 (2008)

ional Application No. PCT/US2017/021405 filed Mar. 8, 2017, which claims priority to U.S. Provisional Application Ser. No. 62/305,194, filed on Mar. 8, 2016, entitled "COMPOSITIONS FOR CHARACTERIZING DEVELOPMENT OF ESOPHAGEAL ADENOCARCINOMA IN PATIENTS AND METHODS OF USE THEREOF", the entire content of each of which is hereby incorporated by reference in its entirety.

COMPOSITIONS FOR CHARACTERIZING DEVELOPMENT OF ESOPHAGEAL ADENOCARCINOMA IN PATIENTS AND METHODS OF USE THEREOF

CROSS REFERENCE TO RELATED APPLICATION

This application claims priority to International Application No. PCT/US2017/021405 filed Mar. 8, 2017, which claims priority to U.S. Provisional Application Ser. No. 62/305,194, filed on Mar. 8, 2016, entitled "COMPOSITIONS FOR CHARACTERIZING DEVELOPMENT OF ESOPHAGEAL ADENOCARCINOMA IN PATIENTS AND METHODS OF USE THEREOF", the entire content of each of which is hereby incorporated by reference in its entirety.

FIELD OF THE INVENTION

The field of invention relates to compositions for characterizing development of esophageal adenocarcinoma in a patient.

BACKGROUND

Chronic regurgitation of highly acidic stomach fluids into the esophagus results in development of a specialized tissue called Barrett's epithelium (BE) at the distal segment of the esophagus and at the junction of esophagus and stomach. BE is known to progress to a morbid cancer known as Esophageal adenocarcinoma (EA). Within 5 years of diagnosis, 90% of the patients die from EA. Patients with BE are at a 120 fold higher risk of developing EA in a slow progression of disease from BE to low grade dysplasia, from low grade dysplasia to high grade dysplasia, and ultimately from high grade dysplasia into EA over several years. Slow progression of the disease allows time for medical intervention to prevent or slow down cancer development.

SUMMARY OF THE INVENTION

In some embodiments, the present invention provides a method, comprising:
 (a) obtaining a sample of an esophageal tissue from a subject,
 wherein the sample of the esophageal tissue comprises or is suspected of comprising a first translocation, a second translocation, a third translocation, or any combination thereof,
 wherein
  (i) the first translocation comprises a break of chromosome 2 (chr2) and a fusion of the break of chr2 with chromosome 10 (chr10),
  (ii) the second translocation comprises a break of chr10 and a fusion of the break of chr10 with chromosome 16 (chr16), and
  (iii) the third translocation comprises a break of chr16 and a fusion of the break of chr16 with chr2; and
 (b) detecting in the sample of esophageal tissue whether the first translocation is present, whether the second translocation is present, whether the third translocation is present, or any combination thereof, by contacting the sample of esophageal tissue with a first detectably labeled probe, a second detectably labeled probe, a third detectably labeled probe, or any combination thereof, and detecting binding between:
  (i) the first detectably labeled probe and the first translocation,
  (ii) the second detectably labeled probe and the second translocation,
  (iii) the third detectably labeled probe and the third translocation, or
  (iv) any combination thereof.

In some embodiments, the method further comprises: (c) diagnosing the subject with a predisposition for esophageal adenocarcinoma (EA) or EA when the presence of the first translocation, the second translocation, the third translocation, or any combination thereof, is detected.

In some embodiments, the sample of the esophageal tissue comprises or is suspected of comprising the first translocation, the second translocation, the third translocation, or any combination thereof.

In some embodiments, the present invention provides a method, comprising:
 (a) obtaining a sample of an esophageal tissue from a subject, wherein the sample of the esophageal tissue comprises or is suspected of comprising a break of chromosome 2 (chr2), a break of chromosome 10 (chr10), a break of chromosome 16 (chr16), or any combination thereof, and
 (b) detecting in the sample of esophageal tissue whether the break of chr2 is present, whether the break of chr10 is present, whether the break of chr16 is present, or any combination thereof, by contacting the sample of esophageal tissue with a first detectably labeled probe, a second detectably labeled probe, a third detectably labeled probe, or any combination thereof, and detecting binding between:
  (i) the first detectably labeled probe and the break of chr2,
  (ii) the second detectably labeled probe and the break of chr10,
  (iii) the third detectably labeled probe and the break of chr16, or
  (iv) any combination thereof.

In some embodiments, the method further comprises: (c) diagnosing the subject with a predisposition for esophageal adenocarcinoma (EA) or EA when the presence of the break of chr2, the break of chr10, the break of chr16, or any combination thereof, is detected.

In some embodiments, the sample of the esophageal tissue comprises or is suspected of comprising the break of chr2, the break of chr10, the break of chr16, or any combination thereof.

In some embodiments, the sample of the esophageal tissue is fresh, frozen, or paraffin embedded.

In some embodiments, the first detectably labeled probe comprises SEQ ID:1, SEQ ID:2, or a combination thereof. In some embodiments, the second detectably labeled probe comprises SEQ ID:3, SEQ ID:4, SEQ ID:5, or any combination thereof. In some embodiments, the third detectably labeled probe comprises SEQ ID:6, SEQ ID:7, SEQ ID:8, or any combination thereof.

In some embodiments, the subject has gastroesophageal reflux disease. In some embodiments, the subject has Barrett's esophagus. In some embodiments, the subject has low grade dysplasia. In some embodiments, the subject has high grade dysplasia. In some embodiments, the subject has esophageal adenocarcinoma.

In some embodiments, the detecting is performed using a microscope or flow cytometry. In some embodiments, the detectably labeled probe is detectable by fluorescence.

In some embodiments, the present invention provides a composition, comprising a detectably labeled probe comprising SEQ ID:1, SEQ ID:2, SEQ ID:3, SEQ ID:4 SEQ ID:5, SEQ ID:6, SEQ ID:7, SEQ ID:8, or any combination thereof.

In some embodiments, the present invention provides a kit, comprising:
  (i) SEQ ID:1, SEQ ID:2, SEQ ID:3, SEQ ID:4, SEQ ID:5, SEQ ID:6, SEQ ID:7, SEQ ID:8, or any combination thereof, and
  (ii) instructions for performing an assay for detecting:
    (a) a first translocation, a second translocation, a third translocation, or any combination thereof, wherein
      (i) the first translocation comprises a break of chromosome 2 (chr2) and a fusion of the break of chr2 with chromosome 10 (chr10),
      (ii) the second translocation comprises a break of chr10 and a fusion of the break of chr10 with chromosome 16 (chr16), and
      (iii) the third translocation comprises a break of chr16 and a fusion of the break of chr16 with chr2; or
    (b) a break at chr2, a break at chr10, a break at chr16, or any combination thereof.

In some embodiments, the kit further comprises a negative control, wherein the negative control does not contain a chromosomal break.

In some embodiments, the kit further comprises a positive control, wherein the positive control has a break at chr2, a break at chr10, a break at chr16, or any combination thereof. In some embodiments, the kit further comprises a positive control, wherein the positive control has a first translocation, a second translocation, a third translocation, or any combination thereof, wherein
  (i) the first translocation comprises a break of chromosome 2 (chr2) and a fusion of the break of chr2 with chromosome 10 (chr10),
  (ii) the second translocation comprises a break of chr10 and a fusion of the break of chr10 with chromosome 16 (chr16), and
  (iii) the third translocation comprises a break of chr16 and a fusion of the break of chr16 with chr2.

BRIEF DESCRIPTION OF THE FIGURES

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

FIG. 2A shows a diagrammatic view of translocation events, FIG. 2B illustrates Fluorescent in-situ hybridization (FISH) signal from paraffin embedded tumor tissue; FIG. 2C shows an enhanced view of the FISH signal from FIG. 2B. FIGS. 2D and 2E show FISH performed with probes for breakpoints on transformed cells derived from the BEC model and carrying the translocations.

Figure 1:
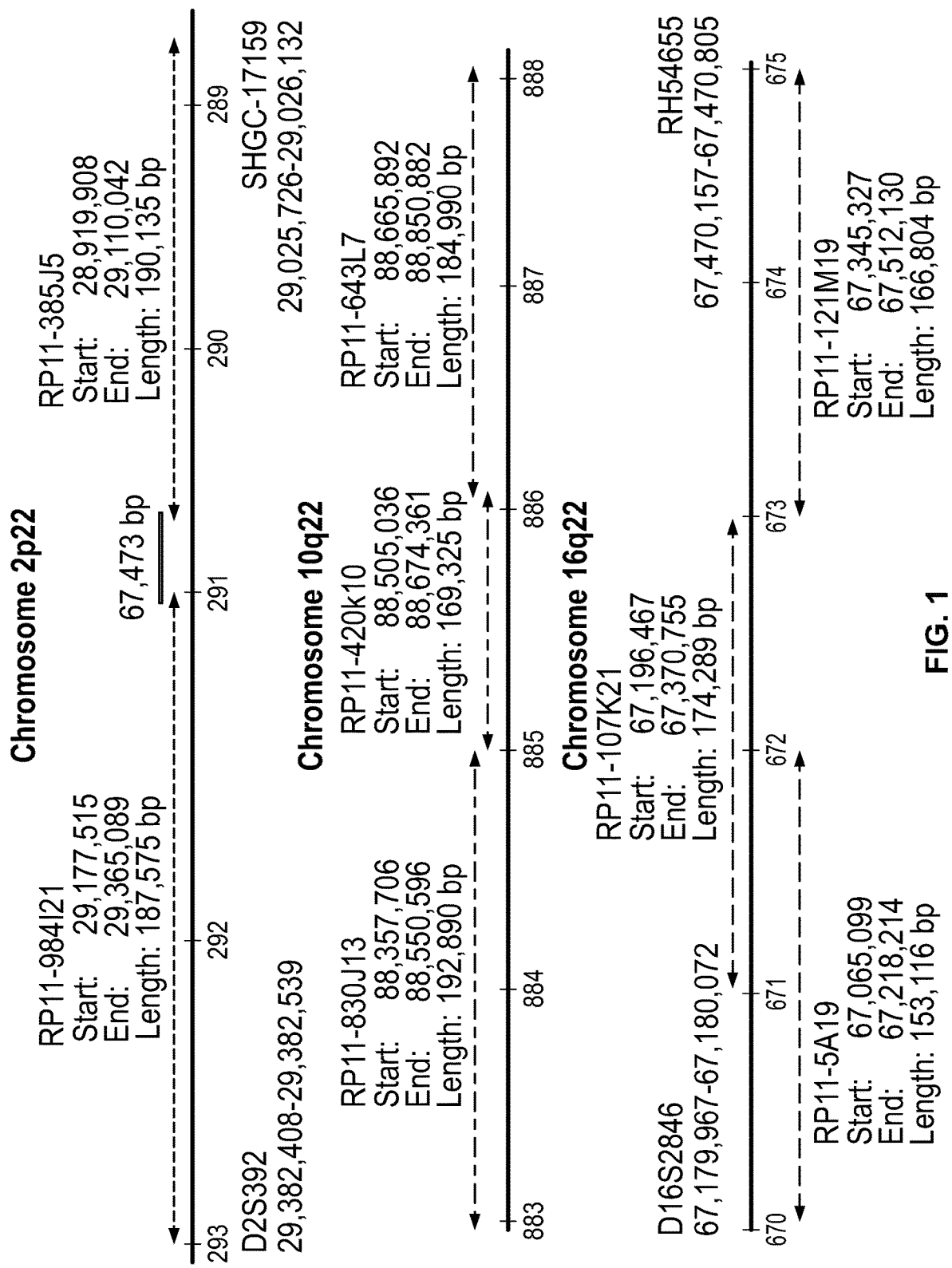
FIG. 1 shows a detailed map around the breakpoint of chromosomes 2, 10, and 16, which is used in some embodiments of the methods of the present invention.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Each of the embodiments and aspects of the present disclosure can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Method of Detection

As used herein, a "break apart probe" or "detectably labeled probe" (e.g., a first detectably labeled probe, a second detectably labeled probe, a third detectably labeled probe, etc.) refers to a DNA probe designed to detect the translocation between segments of chromosomes. Break apart probes can bind to the same chromosome pair in at least two locations, and, when a translocation occurs the probe not only remains on the chromosome pair but is also detected on at least one separate chromosome. As a non-limiting example, the break apart probe (or "probe") for Chromosome 2 ("chr2") of the present invention includes two DNA segments. As a non-limiting example, the break apart probe (or "probe") for Chromosome 10 ("chr10") of the present invention includes two DNA segments. As another non-limiting example, the break apart probe (or "probe") for Chromosome 16 ("chr16") of the present invention includes two DNA segments. As another non-limiting example, since each chromosome of chr2, chr10, or chr16 comprises paired chromosomes, the break apart probe (set of two DNA segments) is configured to identify and bind to two locations; (e.g., one location for each of the pair of chromosomes in a normal pair of chromosomes) thus, when a translocation occurs and a segment of one of the chromosomes of the pair moves to another chromosome or to a different pair of chromosomes, the probe can bind to the separated segment of the broken chromosome.

As used herein, a "chromosomal break" or a "break" refers to a chromosomal abnormality in which a portion of a chromosome that has broken away and is no longer connected to the chromosome. In some embodiments, the size of the break is 50% of the chromosome or less (e.g., but not limited to, 40%, 30%, 20%, 10%, etc., of the full chromosome).

As used herein, "complementarity" refers to a relationship between two DNA sequences, such that when they are aligned antiparallel to each other, the nucleotide bases at each position in the sequences will be complementary (e.g., the reverse or "mirror-image"). The degree of complementarity between two nucleic acid strands may vary, from complete complementarity (e.g., each nucleotide is across from its opposite) to no complementarity (e.g., each nucleotide is not across from its opposite) and determines the stability of the sequences to be together.

As used herein, "fluorescence in situ hybridization" or "FISH" refers to a cytogenetic technique that uses at least one fluorescent probe (e.g., the detectably labeled probe comprising SEQ ID:1, SEQ ID:2, SEQ ID:3, SEQ ID:4 SEQ ID:5, SEQ ID:6, SEQ ID:7, SEQ ID:8, or any combination thereof) that binds to only those parts of the chromosome with a high degree of sequence complementarity.

As used herein, "flow cytometry" refers to a technology used to analyze the physical and chemical characteristics of particles in a fluid as it passes through at least one laser. Cell components (e.g., at least one chromosome) are fluorescently labelled and then excited by the laser to emit light at varying wavelengths.

As used herein, "fusion" or "fuse" refers to the process in which a portion of a chromosome breaks away from the chromosome and chemically attaches to a separate chromosome.

As used herein, the term "sample" refers to any composition containing or presumed to contain nucleic acid (DNA) from an individual. In the context of the present disclosure, a tissue biopsy may be used, including paraffin embedded tissues or tissues collected and preserved in the course of a pathologic or forensic investigation. Samples also may include constituents and components of esophageal cells or in vitro cultures of cells obtained from an individual.

As used herein, a "translocation" refers to a chromosome abnormality caused by rearrangement of parts between non-homologous chromosomes. Translocations can be balanced (e.g., in an even exchange of material with no genetic information extra or missing, and ideally full functionality) or unbalanced (e.g., where the exchange of chromosome material is unequal resulting in extra or missing genes. Translocations can be reciprocal (balanced or unbalanced) or nonreciprocal (balanced or unbalanced). Reciprocal translocations are typically an exchange of material between non-homologous chromosomes.

In some embodiments, the present invention provides a method, comprising:
  (a) obtaining a sample of an esophageal tissue from a subject,
  wherein the sample of the esophageal tissue comprises or is suspected of comprising a first translocation, a second translocation, a third translocation, or any combination thereof,
  wherein
    (i) the first translocation comprises a break of chromosome 2 (chr2) and a fusion of the break of chr2 with chromosome 10 (chr10),
    (ii) the second translocation comprises a break of chr10 and a fusion of the break of chr10 with chromosome 16 (chr16), and
    (iii) the third translocation comprises a break of chr16 and a fusion of the break of chr16 with chr2; and
  (b) detecting in the sample of esophageal tissue whether the first translocation is present, whether the second translocation is present, whether the third translocation is present, or any combination thereof, by contacting the sample of esophageal tissue with a first detectably labeled probe, a second detectably labeled probe, a third detectably labeled probe, or any combination thereof, and detecting binding between:
    (i) the first detectably labeled probe and the first translocation,
    (ii) the second detectably labeled probe and the second translocation,
    (iii) the third detectably labeled probe and the third translocation, or
    (iv) any combination thereof.

In some embodiments, the method further comprises: (c) diagnosing the subject with a predisposition for esophageal adenocarcinoma (EA) or EA when the presence of the first translocation, the second translocation, the third translocation, or any combination thereof, is detected.

In some embodiments, the sample of the esophageal tissue comprises or is suspected of comprising the first translocation, the second translocation, the third translocation, or any combination thereof.

In some embodiments, the present invention provides a method, comprising:
  (a) obtaining a sample of an esophageal tissue from a subject,
  wherein the sample of the esophageal tissue comprises or is suspected of comprising a break of chromosome 2 (chr2), a break of chromosome 10 (chr10), a break of chromosome 16 (chr16), or any combination thereof, and
  (b) detecting in the sample of esophageal tissue whether the break of chr2 is present, whether the break of chr10 is present, whether the break of chr16 is present, or any combination thereof, by contacting the sample of esophageal tissue with a first detectably labeled probe, a second detectably labeled probe, a third detectably labeled probe, or any combination thereof, and detecting binding between:
(i) the first detectably labeled probe and the break of chr2,
(ii) the second detectably labeled probe and the break of chr10,
(iii) the third detectably labeled probe and the break of chr16, or
(iv) any combination thereof.

In some embodiments, the method further comprises: (c) diagnosing the subject with a predisposition for esophageal adenocarcinoma (EA) or EA when the presence of the break of chr2, the break of chr10, the break of chr16, or any combination thereof, is detected.

In some embodiments, the sample of the esophageal tissue comprises or is suspected of comprising the break of chr2, the break of chr10, the break of chr16, or any combination thereof.

In some embodiments, the first detectably labeled probe comprises SEQ ID:1, SEQ ID:2, or a combination thereof. In some embodiments, the second detectably labeled probe comprises SEQ ID:3, SEQ ID:4, SEQ ID:5, or any combination thereof. In some embodiments, the third detectably labeled probe comprises SEQ ID:6, SEQ ID:7, SEQ ID:8, or any combination thereof.

In some embodiments, a first detectably labeled probe comprises chr2-RP11-385J5 (nucleotides 28919908-29110042) [SEQ ID:1] and/or chr2-RP11-984121 (nucleotides 29177515-29365089) [SEQ ID:2]. In some embodiments, a second detectably labeled probe comprises chr10-RP11-643L7 (nucleotides 88665892-88850882) [SEQ ID:3], chr10-RP11-420k10 (nucleotides 88505036-88674361) [SEQ ID:4], chr10-RP11-830J13 (nucleotides 88357706-88550596) [SEQ ID:5], or any combination thereof. In some embodiments, a third detectably labeled probe comprises chr16-RP11-107K21 (nucleotides 67196467-67370755) [SEQ ID:6], chr16-RP11-121M19 (nucleotides 67345327-67512130) [SEQ ID:7], chr16-RP11-5A19 (nucleotides 67065099-67218214) [SEQ ID:8], or any combination thereof.

In some embodiments, the detecting is performed using a microscope or flow cytometry. In some embodiments, the detectably labeled probe is detectable by fluorescence.

In some embodiments, the flow cytometry is performed as described in Rabinovitch et al., "Predictors of progression in Barrett's Esophagus III: Base line Flow Cytometric Variables" (2001) American Journal of Gastroenterology 96:11, which is incorporated by reference herein in its entirety.

In some embodiments, the flow cytometry is performed as described in Raponi et al., "An accurate and rapid flow cytometric diagnosis or BCR-ABL positive acute lymphoblastic leukemia" Haematologica (2009) 94(12): 1767-1770, which is incorporated by reference herein in its entirety.

In some embodiments, the detectably labeled probe is used in fluorescence in situ hybridization (FISH).

In some embodiments, the present invention is a method, comprising: (a) obtaining a sample of esophageal tissue suspected of comprising a first translocation, a second translocation, and a third translocation from the human subject, wherein the sample of the esophageal tissue comprises or is suspected of comprising the first translocation, the second translocation, and the third translocation, wherein the first translocation comprises a break of a short arm of chromosome 2 (chr2) and a fusion of the break of the short arm of chr2 with a long arm of chromosome 10 (chr10), the second translocation comprises a break of the long arm of chr10 and a fusion of the long arm of chr10 with a long arm of chromosome 16 (chr16), the third translocation comprises a break of a long arm of chr16 and a fusion of the long arm of chr16 with the short arm of chr2; (b) detecting the presence of the first translocation, the second translocation, and the third translocation in the sample of esophageal tissue, whereby the presence of the first translocation, the presence of the second translocation, and the presence of the third translocation in the sample of esophageal tissue is indicative of a predisposition to development of esophageal adenocarcinoma or presence of EA, wherein detecting the presence of the first translocation, the second translocation, and the third translocation is by application of a first detectably labeled probe, a second detectably labeled probe, and a third detectably labeled probe, where the first detectably labeled probe, the second detectably labeled probe, and the third detectably labeled probe each hybridize to the first translocation, the second translocation, and the third translocation and (c) characterizing the esophageal tissue as developing esophageal adenocarcinoma or not developing esophageal adenocarcinoma. In some embodiments, characterizing the esophageal tissue as developing esophageal adenocarcinoma includes identifying the first detectably labeled probe, the second detectably labeled probe, and the third detectably labeled probe each hybridizing to the first translocation, the second translocation, and the third translocation, so as to result in three positive hybridization results. In some embodiments, characterizing the esophageal tissue as not developing esophageal adenocarcinoma includes identifying the first detectably labeled probe, the second detectably labeled probe, and the third detectably labeled probe, where at least one of the first detectably labeled probe, the second detectably labeled probe, and the third detectably labeled probe does not hybridize to the first translocation, the second translocation, and/or the third translocation, so as to result in no positive hybridization results.

In some embodiments, the present invention is a method, comprising: (a) obtaining a sample of esophageal tissue suspected of comprising a first translocation and a second translocation from a human subject, wherein the sample of the esophageal tissue comprises or is suspected of comprising the first translocation and the second translocation, wherein the first translocation comprises a break of a short arm of chromosome 2 (chr2) and a fusion of chr2 with a long arm of chromosome 10 (chr10), the second translocation comprises a break of the long arm of chr10 and a fusion of chr10 with a short arm of chr2; (b) detecting the presence of the first translocation and the second translocation in the sample of esophageal tissue, whereby the presence of the first translocation and the presence of the second translocation in the sample of esophageal tissue is indicative of a predisposition to development of esophageal adenocarcinoma or presence of EA, wherein detecting the presence of the first translocation and the second translocation is by application of a first detectably labeled probe and a second detectably labeled probe, where the first detectably labeled probe and the second detectably labeled probe each hybridize to the first translocation and the second translocation, and (c) characterizing the esophageal tissue as developing esophageal adenocarcinoma or not developing esophageal adenocarcinoma. In some embodiments, characterizing the esophageal tissue as developing esophageal adenocarcinoma includes identifying the first detectably labeled probe and the second detectably labeled probe each hybridizing to the first translocation and the second translocation, so as to result in two positive hybridization results. In some embodiments, characterizing the esophageal tissue as not developing esophageal adenocarcinoma includes identifying the first detectably labeled probe and the second detectably labeled probe, where at least one of the first detectably labeled probe and the second detectably labeled probe does not hybridize to the first translocation and/or the second translocation, so as to result in no positive hybridization results.

In some embodiments, the present invention is a method, comprising: (a) obtaining a sample of esophageal tissue suspected of comprising a first translocation and a second translocation from the human subject, wherein the sample of the esophageal tissue comprises or is suspected of comprising the first translocation and the second translocation, wherein the first translocation comprises a break of a short arm of chromosome 2 (chr2) and a fusion of chr2 with a long arm of chromosome 16 (chr16) and the second translocation comprises a break of a long arm of chr16 and a fusion of the short arm of chr2; (b) detecting the presence of the first translocation and the second translocation in the sample of esophageal tissue, whereby the presence of the first translocation and the presence of the second translocation in the sample of esophageal tissue is indicative of a predisposition to development of esophageal adenocarcinoma or presence of EA, wherein detecting the presence of the first translocation and the second translocation is by application of a first detectably labeled probe and a second detectably labeled probe, where the first detectably labeled probe and the second detectably labeled probe each hybridize to the first translocation and the second translocation, and (c) characterizing the esophageal tissue as developing esophageal adenocarcinoma or not developing esophageal adenocarcinoma. In some embodiments, characterizing the esophageal tissue as developing esophageal adenocarcinoma includes identifying the first detectably labeled probe and the second detectably labeled probe each hybridizing to the first translocation and the second translocation, so as to result in two positive hybridization results. In some embodiments, characterizing the esophageal tissue as not developing esophageal adenocarcinoma includes identifying the first detectably labeled probe and the second detectably labeled probe, where at least one of the first detectably labeled probe and the second detectably labeled probe does not hybridize to the first translocation and/or the second translocation, so as to result in no positive hybridization results.

In some embodiments, the present invention is a method, comprising: (a) obtaining a sample of esophageal tissue suspected of comprising a first translocation, a second translocation, and a third translocation from the human subject, wherein the sample of the esophageal tissue comprises or is suspected of comprising the first translocation, the second translocation, and the third translocation, wherein the first translocation comprises a break of a long arm of chr10 and a fusion of chr10 with a long arm of chromosome 16 (chr16), the second translocation comprises a break of a long arm of chr16 and a fusion of long arm of chr10; (b) detecting the presence of the first translocation and the second translocation in the sample of esophageal tissue, whereby the presence of the first translocation and the presence of the second translocation in the sample of esophageal tissue is indicative of a predisposition to development of esophageal adenocarcinoma or presence of EA, wherein detecting the presence of the first translocation and the second translocation is by application of a first detectably labeled probe and a second detectably labeled probe, where the first detectably labeled probe and the second detectably labeled probe each hybridize to the first translocation and the second translocation and (c) characterizing the esophageal tissue as developing esophageal adenocarcinoma or not developing esophageal adenocarcinoma. In some embodiments, characterizing the esophageal tissue as developing esophageal adenocarcinoma includes identifying the first detectably labeled probe and the second detectably labeled probe each hybridizing to the first translocation comprising a break of the first chromosome and the second translocation, comprising a break of the first chromosome so as to result in three positive hybridization results, wherein a third positive hybridization result is identified as the break and the break may remain separate from all chromosomes or fuze with a new chromosome. In some embodiments, characterizing the esophageal tissue as not developing esophageal adenocarcinoma includes identifying the first detectably labeled probe and the second detectably labeled probe, where at least one of the first detectably labeled probe and the second detectably labeled probe hybridize to the complementary sequences on the chromosomes and lead to only two positive hybridization signals per probe.

In some embodiments, a first detectably labeled probe comprises chr2-RP11-385J5 (nucleotides 28919908-29110042) [SEQ ID:1], and chr2-RP11-984121 (nucleotides 29177515-29365089) [SEQ ID:2]. In some embodiments, a second detectably labeled probe comprises chr10-RP11-643L7 (nucleotides 88665892-88850882) [SEQ ID:3], chr10-RP11-420k10 (nucleotides 88505036-88674361) [SEQ ID:4], and chr10-RP11-830J13 (nucleotides 88357706-88550596) [SEQ ID:5]. In some embodiments, a third detectably labeled probe comprises chr16-RP11107K21 (nucleotides 67196467-67370755) [SEQ ID:6], chr16-RP11-121M19 (nucleotides 67345327-67512130) [SEQ ID:7], and chr16-RP11-5A19 (nucleotides 67065099-67218214) [SEQ ID:8].

In some embodiments, characterizing the esophageal tissue as developing esophageal adenocarcinoma can refer to an increase in a subject's likelihood of developing esophageal adenocarcinoma, where the increase can range from, e.g., but not limited to, between 10%-100% (e.g., but not limited to, 10%, 20%, 30%, 40%, 50%, 60%, 70%, 80%, 90%, 100%) when compared with a normal sample (e.g., but not limited to, a sample of esophageal tissue retrieved from a patient not diagnosed with BE).

In some embodiments, the increase in the likelihood of developing esophageal adenocarcinoma can be between 10-90% when compared with a normal sample (e.g., but not limited to, a sample of esophageal tissue retrieved from a patient not diagnosed with BE). In some embodiments, the increase in the likelihood of developing esophageal adenocarcinoma can be between 10-80% when compared with a normal sample (e.g., but not limited to, a sample of esophageal tissue retrieved from a patient not diagnosed with BE). In some embodiments, the increase in the likelihood of developing esophageal adenocarcinoma can be between 10-70% when compared with a normal sample (e.g., but not limited to, a sample of esophageal tissue retrieved from a patient not diagnosed with BE). In some embodiments, the increase in the likelihood of developing esophageal adenocarcinoma can be between 10-60% when compared with a normal sample (e.g., but not limited to, a sample of esophageal tissue retrieved from a patient not diagnosed with BE). In some embodiments, the increase in the likelihood of developing esophageal adenocarcinoma can be between 10-50% when compared with a normal sample (e.g., but not limited to, a sample of esophageal tissue retrieved from a patient not diagnosed with BE). In some embodiments, the increase in the likelihood of developing esophageal adenocarcinoma can be between 10-40% when compared with a normal sample (e.g., but not limited to, a sample of esophageal tissue retrieved from a patient not diagnosed with BE). In some embodiments, the increase in the likelihood of developing esophageal adenocarcinoma can be between 10-30% when compared with a normal sample (e.g., but not limited to, a sample of esophageal tissue retrieved from a patient not diagnosed with BE). In some embodiments, the increase in the likelihood of developing esophageal adenocarcinoma can be between 10-20% when compared with a normal sample (e.g., but not limited to, a sample of esophageal tissue retrieved from a patient not diagnosed with BE).

In some embodiments, the increase in the likelihood of developing esophageal adenocarcinoma can be between 20-100% when compared with a normal sample (e.g., but not limited to, a sample of esophageal tissue retrieved from a patient not diagnosed with BE). In some embodiments, the increase in the likelihood of developing esophageal adenocarcinoma can be between 30-100% when compared with a normal sample (e.g., but not limited to, a sample of esophageal tissue retrieved from a patient not diagnosed with BE). In some embodiments, the increase in the likelihood of developing esophageal adenocarcinoma can be between 40-100% when compared with a normal sample (e.g., but not limited to, a sample of esophageal tissue retrieved from a patient not diagnosed with BE). In some embodiments, the increase in the likelihood of developing esophageal adenocarcinoma can be between 50-100% when compared with a normal sample (e.g., but not limited to, a sample of esophageal tissue retrieved from a patient not diagnosed with BE). In some embodiments, the increase in the likelihood of developing esophageal adenocarcinoma can be between 60-100% when compared with a normal sample (e.g., but not limited to, a sample of esophageal tissue retrieved from a patient not diagnosed with BE). In some embodiments, the increase in the likelihood of developing esophageal adenocarcinoma can be between 70-100%. In some embodiments, the increase in the likelihood of developing esophageal adenocarcinoma can be between 80-100% when compared with a normal sample (e.g., but not limited to, a sample of esophageal tissue retrieved from a patient not diagnosed with BE). In some embodiments, the increase in the likelihood of developing esophageal adenocarcinoma can be between 90-100% when compared with a normal sample (e.g., but not limited to, a sample of esophageal tissue retrieved from a patient not diagnosed with BE).

In some embodiments, the increase in the likelihood of developing esophageal adenocarcinoma can be between 20-90% when compared with a normal sample (e.g., but not limited to, a sample of esophageal tissue retrieved from a patient not diagnosed with BE). In some embodiments, the increase in the likelihood of developing esophageal adenocarcinoma can be between 30-80% when compared with a normal sample (e.g., but not limited to, a sample of esophageal tissue retrieved from a patient not diagnosed with BE). In some embodiments, the increase in the likelihood of developing esophageal adenocarcinoma can be between 40-70% when compared with a normal sample (e.g., but not limited to, a sample of esophageal tissue retrieved from a patient not diagnosed with BE). In some embodiments, the increase in the likelihood of developing esophageal adenocarcinoma can be between 50-60% when compared with a normal sample (e.g., but not limited to, a sample of esophageal tissue retrieved from a patient not diagnosed with BE).

Tissue Obtained from a Human Subject

As used herein, "gastroesophageal reflux disease" refers to a digestive disorder that affects the lower esophageal sphincter, the ring of muscle between the esophagus and stomach, where the stomach's contents return into the esophagus.

As used herein, the term "esophageal adenocarcinoma" or "EA" refers to a disease state of a subject, in which the glandular cells present in the lower third of the esophagus, often where they have already transformed to intestinal cell type (a condition known as "Barrett's esophagus").

As used herein, "high grade dysplasia" refers to a subject diagnosed with Barrett's esophagus, where the subject has an increased risk of esophageal adenocarcinoma. High grade dysplasia means that some of the cells contained in the area of Barrett's esophagus look abnormal under the microscope. This is a more advanced pre-cancer of the esophagus than low-grade dysplasia. Subjects diagnosed with high grade dysplasia have a high risk of getting esophageal adenocarcinoma.

As used herein, "low grade dysplasia" refers to a subject diagnosed with Barrett's esophagus, where the subject has an increased risk of esophageal adenocarcinoma. Low-grade dysplasia means that some of the cells look abnormal when seen under the microscope. Subjects diagnosed with low grade dysplasia have an increased risk of getting esophageal adenocarcinoma compared to subjects not diagnosed with low grade dysplasia.

In some embodiments, esophageal tissue is obtained from a biopsy. In some embodiments, esophageal cells are obtained from a biopsy. In some embodiments, esophageal cells are obtained from a sponge biopsy.

In some embodiments, the subject has gastroesophageal reflux disease. In some embodiments, the subject has Barrett's esophagus. In some embodiments, the subject has low grade dysplasia. In some embodiments, the subject has high grade dysplasia. In some embodiments, the subject has esophageal adenocarcinoma.

In some embodiments, the sample of the esophageal tissue is fresh, frozen, or paraffin embedded. In some embodiments, the esophageal tissue can be frozen using liquid nitrogen using standard techniques and then embedded in optimal compound (OCT) compound for making sections (e.g., but not limited to, 5 micron tissue sections) for FISH. In some embodiments, tissue can be fixed in formalin and then embedded in paraffin wax.

Composition for Detecting a Translocation or a Chromosomal Break

In some embodiments, the present invention provides a composition, comprising a detectably labeled probe comprising SEQ ID:1, SEQ ID:2, SEQ ID:3, SEQ ID:4 SEQ ID:5, SEQ ID:6, SEQ ID:7, SEQ ID:8, or any combination thereof.

In some embodiments, a detectably labeled probe comprises chr2-RP11-385J5 (nucleotides 28919908-29110042) [SEQ ID:1], chr2-RP11-984121 (nucleotides 29177515-29365089) [SEQ ID:2], chr10-RP11-643L7 (nucleotides 88665892-88850882) [SEQ ID:3], chr10-RP11-420k10 (nucleotides 88505036-88674361) [SEQ ID:4], chr10-RP11-830J13 (nucleotides 88357706-88550596) [SEQ ID:5], chr16-RP11-107K21 (nucleotides 67196467-67370755) [SEQ ID:6], chr16-RP11-121M19 (nucleotides 67345327-67512130) [SEQ ID:7], chr16-RP11-5A19 (nucleotides 67065099-67218214) [SEQ ID:8], or any combination thereof.

In some embodiments, the detectably labeled probe can be artificially modified to have a detectable label or dye attached thereto and hence is non-naturally occurring. The probe can contain a sequence selected from SEQ ID NO: 1, SEQ ID NO: 2, SEQ ID NO: 3, SEQ ID NO: 4, SEQ ID NO:5 SEQ ID NO:6, SEQ ID NO: 7, and/or SEQ ID NO:8. The detectable label or dye can be covalently, non-covalently, directly, or indirectly attached to the probe. The label can be fluorescent or non-fluorescent (e.g., haptens such as Biotin and Digoxigenin). Commonly used fluorescent labels are Orange 5-TAMRA dUTP, Green 5-Flluorescein dUTP, Red 5-ROX dUTP, and Aqua DY-415 dUTP, These fluorescent labels can be directly detected via, e.g., fluorescence spectroscopy. The DNA probe is labeled by various means, such as, but not limited to, nick translation, random primed labeling, and PCR. Two labeling strategies are commonly used: indirect labeling and direct labeling. For indirect labeling, probes are labeled with modified nucleotides that contain a hapten, whereas direct labeling uses nucleotides that have been directly modified to contain a fluorophore. If the probe has been labeled indirectly, an extra step is required for visualization of the non-fluorescent hapten that uses an enzymatic or immunological detection system, which are known in the art.

In some embodiments, the detectably labeled probe is labeled with a fluorescent label. In some embodiments, the fluorescent label comprises: Orange 5-TAMRA dUTP, Green 5-Flluorescein dUTP, Red 5-ROX dUTP, Aqua DY-415 dUTP, Gold 5-carboxyrhodamine 6G dUTP, or any combination thereof.

In some embodiments, the detectably labeled probe is a fragment of DNA of variable length which can be used to detect the presence and/or location of a DNA target (e.g., a chromosome) that has complementary to the sequence in the detectably labeled probe. In some embodiments, the detectably labeled probe hybridizes to the DNA whose base sequence allows for base pairing due to complementarity between the probe and DNA target. In some embodiments, the DNA target is chr2, chr10, chr16, or any combination thereof.

Kit for Detecting a Translocation or a Chromosomal Break

In some embodiments, the present invention provides a kit, comprising:
(i) SEQ ID:1, SEQ ID:2, SEQ ID:3, SEQ ID:4, SEQ ID:5, SEQ ID:6, SEQ ID:7, SEQ ID:8, or any combination thereof, and
(ii) instructions for performing an assay for detecting:
  (a) a first translocation, a second translocation, a third translocation, or any combination thereof, wherein
    (i) the first translocation comprises a break of chromosome 2 (chr2) and a fusion of the break of chr2 with chromosome 10 (chr10),
    (ii) the second translocation comprises a break of chr10 and a fusion of the break of chr10 with chromosome 16 (chr16), and
    (iii) the third translocation comprises a break of chr16 and a fusion of the break of chr16 with chr2; or
  (b) a break at chr2, a break at chr10, a break at chr16, or any combination thereof.

In some embodiments, the kit further comprises a negative control, wherein the negative control does not contain a chromosomal break. In some embodiments, the kit further comprises a negative control, wherein the negative control does not contain a translocation (e.g., a first translocation, a second translocation, a third translocation, or any combination thereof).

In some embodiments, the kit further comprises a positive control, wherein the positive control has a break at chr2, a break at chr10, a break at chr16, or any combination thereof. In some embodiments, the kit further comprises a positive control, wherein the positive control has a first translocation, a second translocation, a third translocation, or any combination thereof, wherein
  (i) the first translocation comprises a break of chromosome 2 (chr2) and a fusion of the break of chr2 with chromosome 10 (chr10),
  (ii) the second translocation comprises a break of chr10 and a fusion of the break of chr10 with chromosome 16 (chr16), and
  (iii) the third translocation comprises a break of chr16 and a fusion of the break of chr16 with chr2.

In some embodiments, the present invention is a kit which provides a first detectably labeled probe (e.g., but not limited to, SEQ ID:1 and SEQ ID:2), a second detectably labeled probe (e.g., but not limited to, SEQ ID:3, SEQ ID:4, and SEQ ID:5), and a third detectably labeled probe (e.g., but not limited to, SEQ ID:6, SEQ ID:7, and SEQ ID:8), or any combination thereof.

Example: Barrett's Epithelium Carcinogenesis

In an exemplary embodiment, the present invention is a method for characterizing three translocation events involving segments of three human chromosomes (chromosomes 2, 10, and 16) in a disease model of Barrett's epithelium carcinogenesis (BEC). As the BEC model demonstrates, progressive events eventually leading to malignant transformation of hTERT immortalized benign metaplastic BE cells, BAR-T as a result of 5 min/day exposure to acidified (pH4) bile salt, GCDC (Glycocheno-deoxycholic acid, physiological component of gastric refluxate) for 60 weeks (BEC60W). The three-way translocation (chromosomes 2, 10, and 16) was reliably reproduced in replicates of the BEC model and appeared around BEC30W almost 30 weeks before the cells become transformed. This translocation event can be described cytogenetically as t(2;10;16) (p22, q22,q22), and involved break of short arm of chr 2 and fusion with long arm of chr10, break of long arm of chr10 and its fusion with long arm of chr16, break of long arm of chr 16 and fusion with short arm of chr2 (see, e.g., FIG. 2A).

Figure 2A:
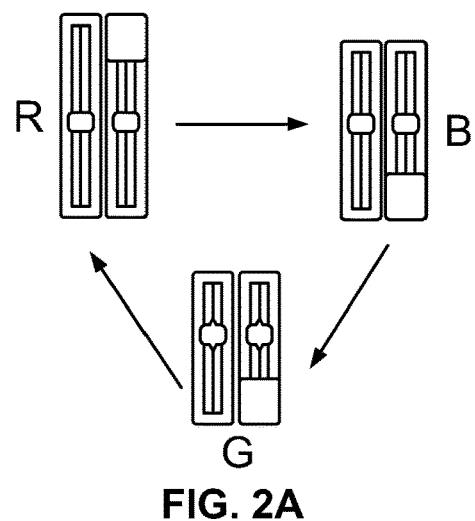
FIGS. 2A-D shows embodiments of the method of the present invention, where
Figure 2B:
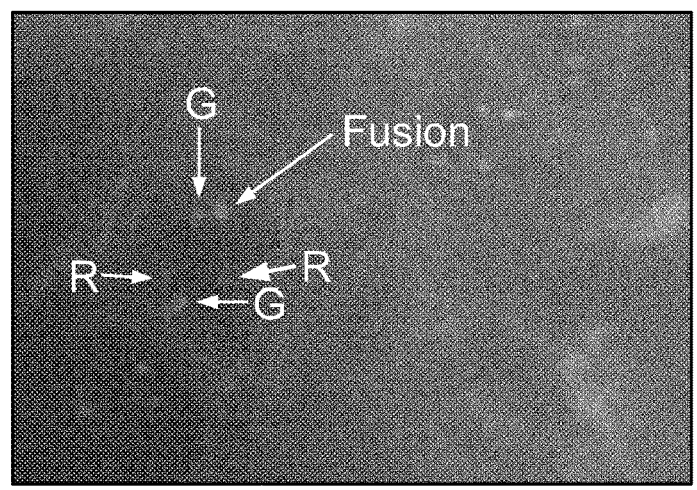
Figure 2C:
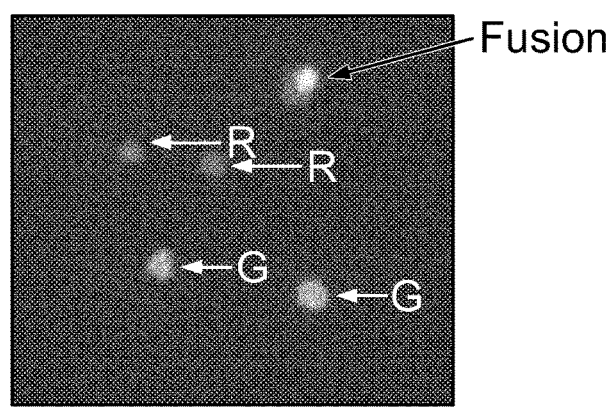
Figure 2D:
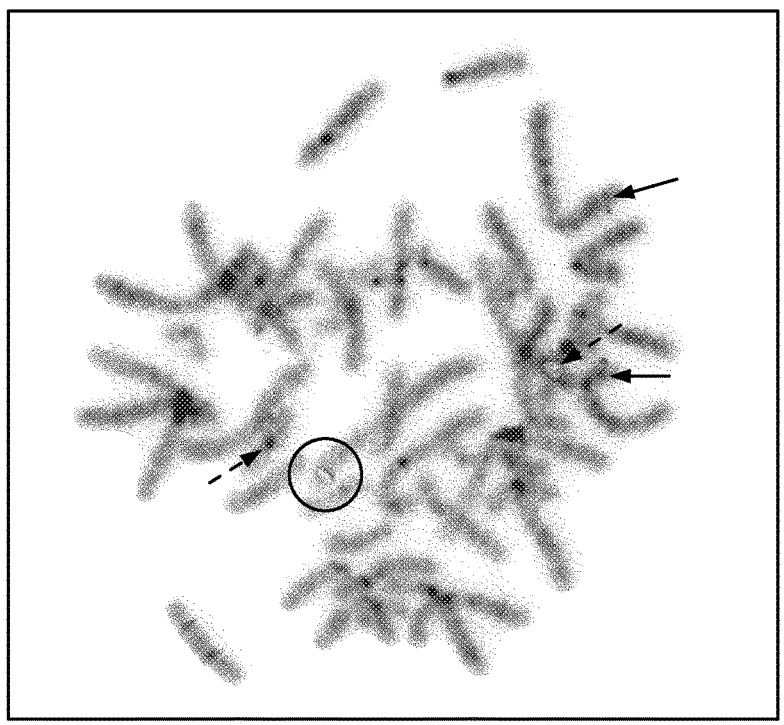
Figure 2E:
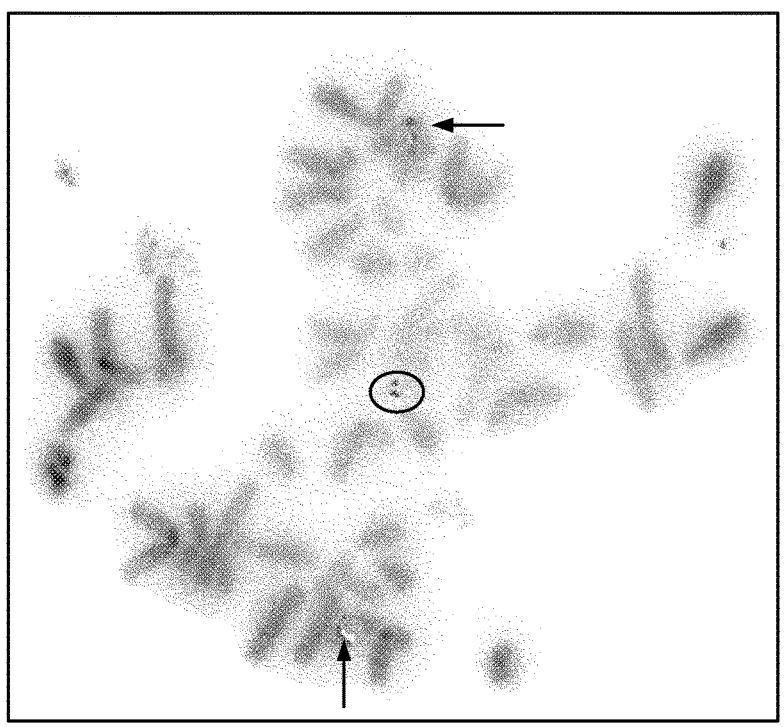

FIG. 2A shows an embodiment of the method of the present invention, showing a diagrammatic view of the translocation events involving breakage and exchange of three chromosome segments t(2; 10; 16) (p22,q22,q22). Chr 2 is red ("R"), chr10 is blue ("B") and chr16 is green ("G"). FIG. 2B shows an embodiment of the method of the present invention, illustrating the Fluorescent in-situ hybridization (i.e., "FISH") signal from paraffin embedded EA tumor tissue using green ("G") color probe for chr16 and red ("R") for chr2 breakpoints. Figure C shows an embodiment of the method of the present invention, showing an enhanced view of the FISH signal from FIG. 2B and illustrating the fusion of red and green signals in the fifth yellowish dot ("fusion"). This fusion signal proves the presence of the unique translocation event involving chr2 and 16 in the EA tissue. The two red signals are one each from the unbroken homologous chr 2 and the remaining part of the broken chr 2. The two green signals are from the homologous chr 16 and the remaining part of the broken chr16. FIGS. 2D and 2E show FISH performed with probes for chr2 and chr10 breakpoints on BEC40W and BEC60W cells. FIG. 2D shows a break apart probe spanning the translocation breakpoint on chr 2 (solid arrow) and relocation of this probe to chr 10 due to a translocation (dotted arrow, bottom). A break apart probe localizes to the translocation breakpoint on chr 16 (dotted arrows). The fusion of the break segment of chr 16 on chr 2 is circled. FIG. 2E shows a break apart probe on two copies of chr10, marked by two arrows, the fusion of segments of chr2 and chr10 is depicted by a circle.

In some embodiments, the method of the present invention includes using DNA probes for chr 2, 10, and 16 breakpoints for identifying the 3-way translocation (i.e., chr2, chr10, and chr16) in EA tissues. Table 1 shows exemplary tissues tested for a presence of at least one chromosomal fusion.

TABLE 1

EA Tissues Tested:

| Case No. | Pathology Report | Pathology Status | Specimen Preparation Type | QC Result | FISH result |
|---|---|---|---|---|---|
| TISSUES STUDIED | | | | | |
| 8561 | moderately differentiated adenocarcinoma intestinal type with invasion through entire thickness of muscalaris propria | Tumor | Frozen Tissue | Good | positive for fusion |
| 7473 | moderately differentiated adenocarcinoma arising in barrets metaplasia | Tumor | Frozen Tissue | Good | positive for fusion |
| 8268 | moderatelly-differentiated adenocarcinoma of esophagus, arising in a tubulovillous adenoma, in a setting of barrets esophagus | Tumor | Frozen Tissue | Good | positive for fusion |
| 3257 | invasive mod diff mucinous adenocarcinoma | Tumor | Frozen Tissue | Good | positive for fusion |
| TISSUES BEING STUDIED | | | | | expected result |
| 3506 | infiltrating mod diff adenocarcinoma of the gastroesophageal | Tumor | Frozen Tissue | Good | positive for fusion |
| 3928 | poorly diff adenocarcinoma | Tumor | Frozen Tissue | Good | positive for fusion |
| 4449 | invasive mod to poorly diff adenocarcinoma | Tumor | Frozen Tissue | Good | positive for fusion |
| 5634 | moderate to poor focally differentiated invasive adenocarcinoma | Tumor | Frozen Tissue | Good | positive for fusion |
| 7668 | moderately differentiated adenocarcinoma intestinal type, arising in a background of barrets esophagus | Tumor | Frozen Tissue | Good | positive for fusion |
| 3190 | adenocarcinoma mod diff | Tumor | Frozen Tissue | | positive for fusion |
| 3289 | poorly diff adenocarcinoma | Tumor | Frozen Tissue | | positive for fusion |
| 8561 | moderately differentiated adenocarcinoma intestinal type with invasion through entire thickness of muscalaris propria | Normal area surrounding tumor | Frozen Tissue | Good | no fusion signal |
| 7473 | moderately differentiated adenocarcinoma arising in barrets metaplasia | Normal area surrounding tumor | Frozen Tissue | Good | no fusion signal |
| 8268 | moderatelly-differentiated adenocarcinoma of esophagus, arising in a tubulovillous adenoma, in a setting of barrets esophagus | Normal area surrounding tumor | Frozen Tissue | Good | no fusion signal |
| 3257 | invasive mod diff mucinous adenocarcinoma | Normal area surrounding tumor | Frozen Tissue | Good | no fusion signal |

TABLE 1-continued

EA Tissues Tested:

| Case No. | Pathology Report | Pathology Status | Specimen Preparation Type | QC Result | FISH result |
|---|---|---|---|---|---|
| 3506 | infiltrating mod diff adenocarcinoma of the gastroesophageal | Normal area surrounding tumor | Frozen Tissue | Good | no fusion signal |
| 3928 | poorly diff adenocarcinoma | Normal area surrounding tumor | Frozen Tissue | Good | no fusion signal |
| 4449 | invasive mod to poorly diff adenocarcinoma | Normal area surrounding tumor | Frozen Tissue | Good | no fusion signal |
| 5634 | moderate to poor focally differentiated invasive adenocarcinoma | Normal area surrounding tumor | Frozen Tissue | Good | no fusion signal |
| 7668 | moderately differentiated adenocarcinoma intestinal type, arising in a background of barrets esophagus | Normal area surrounding tumor | Frozen Tissue | Good | no fusion signal |
| 3190 | adenocarcinoma mod diff | Normal area surrounding tumor | Frozen Tissue | | no fusion signal |
| 3289 | poorly diff adenocarcinoma | Normal area surrounding tumor | Frozen Tissue | | no fusion signal |

In some embodiments, Bajpai et al. Molecular Cytogenetics 2012, 5:43 discloses methods which may be used in the present invention, and its entire content is hereby incorporated by reference in its entirety.

Methods:

Cell Culture:

BAR-T is an hTERT immortalized cell line derived from a biopsy of benign Barrett's epithelium (methods disclosed in in Jaiswal K R et al., "Characterization of telomerase-immortalized, non-neoplastic, human Barrett's cell line (BAR-T)" Dis Esophagus. 2007; 20(3):256-64, which is hereby incorporated by reference in its entirety) and the different BEC cells are derived from it after B4 exposure, therefore grows in special supplemented keratinocyte medium (KBM2) from Cambrex Bioscience (East Rutherford, N.J., USA) with 5% fetal bovine serum (FBS) containing 1% penicillin/streptomycin. Cells were kept in a humidified incubator with 5% CO2 at 37° C. The bile acid, glycochenodeoxycholic acid, GCDA (Sigma, St. Louis, Mich., USA), was diluted to optimum working concentration of 200 µM and Hydrochloric acid was used to adjust the pH to pH4 (B4). 0.1×10$^6$ cells growing on six-well plates were incubated in B4 for 5 min every day and the cells were then returned to normal KBM2 medium in the incubator. No treatment was done on the day the cells were passed. 5 min was sufficient for induction of signal transduction pathways regulating cellular machinery without cell damage. The control untreated cells were grown in parallel in the KBM2 medium at pH7.4. For chronic exposure, cells were exposed for 5 min every day to B4 for up to 80 weeks and are referred to as BEC0W for parent cells (or BAR-T), BEC20W, BEC30W or BEC60W for 20, 30 or 60 weeks of B4 exposure respectively. These cells were frozen in liquid Nitrogen at different time points and can be revived for additional experiments. The cells were successfully recovered from storage and found to reproduce the transcriptional and chromosomal changes observed in the BEC model at distinct time points. As a non-limiting example, FIG. 3 illustrates this process.

Figure 3:
FIG. 3 shows embodiments of the method of the present invention, showing the time line of changes in the Barrett's epithelial carcinogenesis (BEC) model.

FIG. 3 shows the time line of changes in the Barrett's epithelial carcinogenesis model. Prolonged acid and bile exposure induces a cascade of changes in the BAR-T cells. Induction of colonic phenotype at 2 weeks, genetic and epigenetic changes at about 20 weeks, change in cell shape at 40 weeks, growth in soft agar reminiscent of transformation at 60 weeks and tumor formation in mice at 80 weeks. The chromosomal break and fusion events occur around 30 weeks of acid and bile exposure.

Fluorescent In-Situ Hybridization (FISH)

FISH probes were developed which span the breakpoints on 10q22, 16q22, and 2p22 (e.g., the location is shown in FIG. 1) and each of the three probes (e.g., but not limited to: the probe of chromosome 2 including SEQ IDs:1-2, the probe of chromosome 10 including SEQ IDs: 3-5, and the probe of chromosome 16 including SEQ IDs: 6-8) were confirmed for specificity after comparing the BEC40W and BEC60W cells that carry the translocations to naïve BAR-T cells (i.e., BAR-T cells which have not been previously exposed to acid, e.g., acids at pH4, and/or bile) that do not have this event. For FISH, paraffin embedded tissue slides were first de-paraffinization by placing for 5 min on Hybrite (Vysis) temperature and humidity controlled programmable slide processing system at 90° C. (to melt wax) and then immediately in Citrisolv (Fisher Scientific) and agitated for 10 min. The slides were then transferred to 100% EtOH in room temperature for 5 mins and allowed to air dry. The de-parrafinized slides underwent pre-treatment in 0.1N HCl for 20 min at room temperature followed by a brief rinse in water and 3 mins in wash buffer (2×SSC) followed by 30 mins in Pre-Treatment solution (1M NaSCN) at 80° C. After pretreatment, the slides underwent protease treatment for 1 hr followed by a rinse in 1×PBS (2 min) and then were fixed in Formaldehyde Solution for 5 min and rinsed in PBS again. The slides were then subjected to stepwise dehydration using series of 2 mins dips in 70, 80, 100% EtOH and air dry. The requisite amount of FISH probes were then placed on the tissue section on the slides, sealed, and incubated in the Hybrite. The Hybrite was programmed to denature for 3 mins at 83° C. and hybridize at 37° C. for 20 hours. Following hybridization, slides were washed in 0.4× SSC at 73° C. 3.0 min followed by 2×SSC/0.1% NP40, 30 sec and then stained with DAPI sealed with coverslip and observed under the Olympus BX41 fluorescence microscope or stored in −20° C. freezer. The frozen tissue embedded in optimal cutting temperature compound (OCT) is processed using the same methodology as described herein.

FIG. 1 shows a detailed map of the location of BAC clones around the breakpoint of chromosomes 2, 10, and 16.

Results:

Select BAC Clones can be Used as Specific FISH Probes for the Translocation Event(s) Seen in BEC Model.

The breakpoint on chr2p22 lies between DNA markers: D2S392 and D2S2934 (SHGC-17159) and is spanned by 2 BAC clones: RP11-100C1, and RP11-385J5 (all labeled Red). The breakpoint on chr10q22 is spanned by 3 BAC clones: RP11-1081F9 or RP11-830J13, RP11-420K10, RP11-643L7 (all on Chromosome 10q22). The breakpoint on chr16q22 between DNA markers: D1652846 and RH54655, and is spanned by BAC clones RP11-5A19, RP11-107K21, RP11-121M19 (all green). When the chromosome segments are exchanged, the probes split to the two signals on the different chromosomes as witnessed in FIGS. 2D and 2E. This exchange of segments between chromosomes results in new fusions (one such fusion is shown by yellow color in FIG. 2D chr2p22 and chr16q22)

FISH Probes Detect the Translocation Event in Clinical EA Tissues.

Unlike the metaphase chromosomes seen in cell preparations from cell lines, the tumor tissues mostly have cells in different stages of interphase. Thus the chromosomes are not visible as separate strands and are rather indistinct from each other. With the help of Olympus BX41 fluorescence microscope and meta-systems software, pictures of the probes reveal, break of the chr2 and 16 (represented by red and green dots, one for each pair of chromosomes) and the fusion between segments of chr2 and 16 appears as a yellow dot resulting from juxtaposition of red and green color probes (FIGS. 2B and C).

FISH Probes Detect a Chromosomal Break in Clinical EA Tissues.

Figure 4:
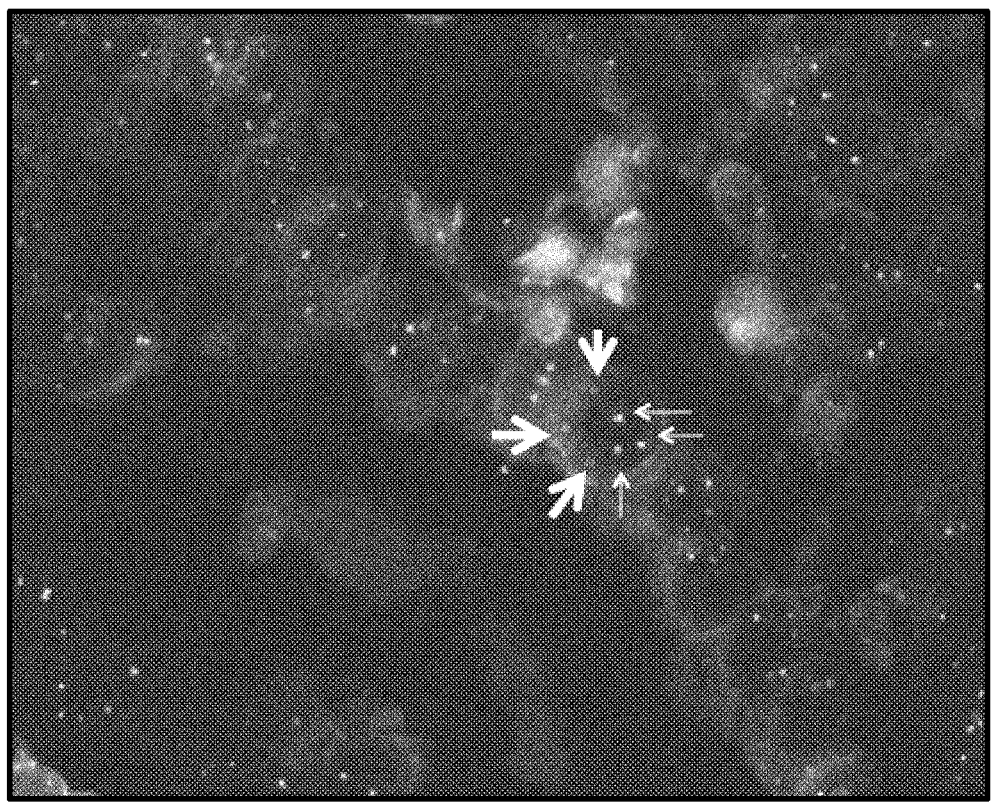
FIG. 4 shows an embodiment of the method of the present invention, where FISH signals are used to identify breaks in chromosomes.

Broken fragments of Chr 2 are shown using thick arrows pointing towards Chr2 fragments, and broken fragments of Chr16 are shown using thin arrows pointing towards Chr16 fragments. While the breakages of chr2 and chr16 occurred, no fusion of either Chr2 or Chr16 was not observed. (FIG. 4) The tumor tissue section was obtained from a resected human esophageal adenocarcinoma with poorly differentiated cells. FIG. 4 depicts a situation when the chr2 and chr16 are both broken to give show three labeled DNA but do not fuse, as yellow signal was not produced by juxtaposition of the red and green color.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11220711B2). An electronic copy of the "Sequence Listing" will also be available from the USPTO upon request and payment of the fee set forth in 37 CFR 1.19(b)(3).

What is claimed is:

1. A method, comprising:
   (a) obtaining a sample of an esophageal tissue from a subject,
   wherein the sample of the esophageal tissue comprises or is suspected of comprising a translocation, wherein the translocation is indicative of a predisposition to development of esophageal adenocarcinoma (EA) or presence of EA,
   wherein the translocation comprises:
      a break of chr16 with a fusion of the break of chr16 with chr2; and
   (b) detecting in the sample of esophageal tissue whether the translocation is present, by contacting the sample of esophageal tissue with at least one detectably labeled probe selected from: SEQ ID NO:1, SEQ ID NO:2, or combinations thereof, and at least one detectably labeled probe selected from: SEQ ID NO:6, SEQ ID NO:7, SEQ ID NO:8, or combination thereof.

2. The method of claim 1, wherein the sample of the esophageal tissue is fresh, frozen, or paraffin embedded.

3. The method of claim 1, wherein the subject has gastroesophageal reflux disease.

4. The method of claim 1, wherein the subject has Barrett's esophagus.

5. The method of claim 1, wherein the subject has low grade dysplasia.

6. The method of claim 1, wherein the subject has high grade dysplasia.

7. The method of claim 1, wherein the detecting is performed using a microscope or flow cytometry.

8. The method of claim 1, wherein the detectably labeled probe is detectable by fluorescence.

* * * * *